United States Patent [19]

Valtchev

[11] Patent Number: 4,681,123

[45] Date of Patent: Jul. 21, 1987

[54] CHORION BIOPSY INSTRUMENT

[76] Inventor: Konstantin L. Valtchev, 43 Cosmic Drive, Don Mills, Toronto, Ontario, Canada

[21] Appl. No.: 925,729

[22] Filed: Oct. 31, 1986

[51] Int. Cl.$^4$ .............................................. A61B 10/00
[52] U.S. Cl. .................................... 128/753; 128/305; 128/754
[58] Field of Search ................................ 128/305–318, 128/749–758

[56] References Cited

U.S. PATENT DOCUMENTS

| | | | |
|---|---|---|---|
| 1,867,624 | 7/1932 | Hoffman | 128/305 |
| 3,401,684 | 9/1968 | Dremann | 128/752 |
| 3,598,088 | 7/1971 | Southamp | 128/305 |
| 3,606,878 | 9/1971 | Kellogg, Jr. | 123/55 A |
| 3,844,272 | 10/1974 | Banko | 128/305 |
| 3,990,453 | 11/1976 | Douugs et al. | 128/305 |
| 4,445,509 | 5/1984 | Auth | 128/305 |
| 4,600,014 | 7/1986 | Beraka | 128/754 |

Primary Examiner—Kyle L. Howell
Assistant Examiner—Max F. Hindenburg
Attorney, Agent, or Firm—Henderson & Sturm

[57] ABSTRACT

A chorion biopsy instrument for sampling chorion tissue including a housing and first and second telescoping tubes with the first tube being closed at one end thereof and having an opening on one side near the closed end. The second outer tube has a cutting edge which slides along the exterior of the first tube. A mechanism is provided for moving the second tube with respect to the first tube between a first position wherein the second tube covers the opening in the first tube and a second position wherein said second tube does not cover the opening in the first tube. A syringe is fluidly connected to a first passageway through the first tube and a bottle of culture medium is fluidly connected to a second passageway leading through the housing, between the two tubes, with the opening in the first tube connecting the first passageway to the second passageway when the tubes are in the first relative position thereof.

4 Claims, 6 Drawing Figures

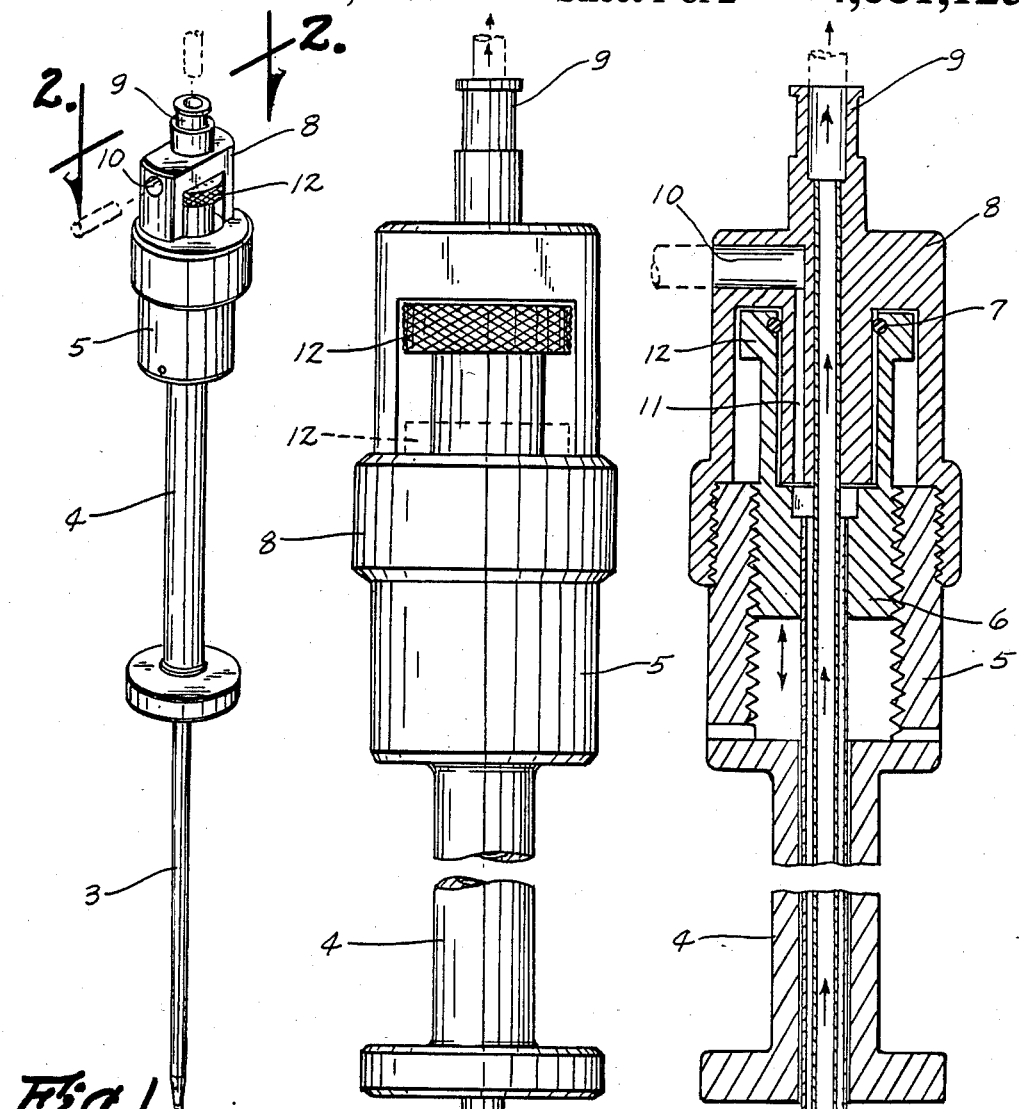
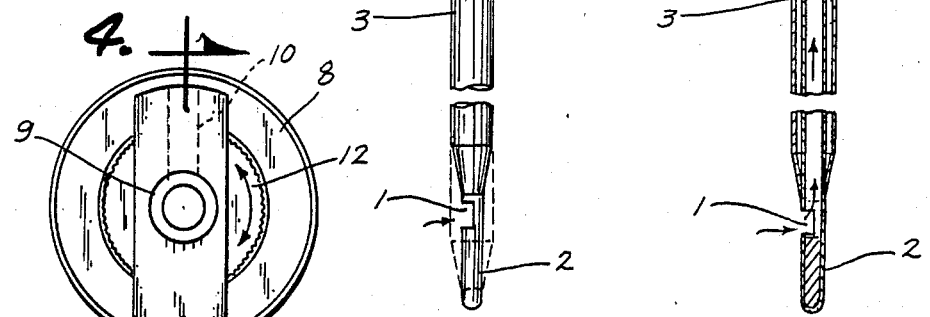
Fig. 1　Fig. 2　Fig. 3　Fig. 4

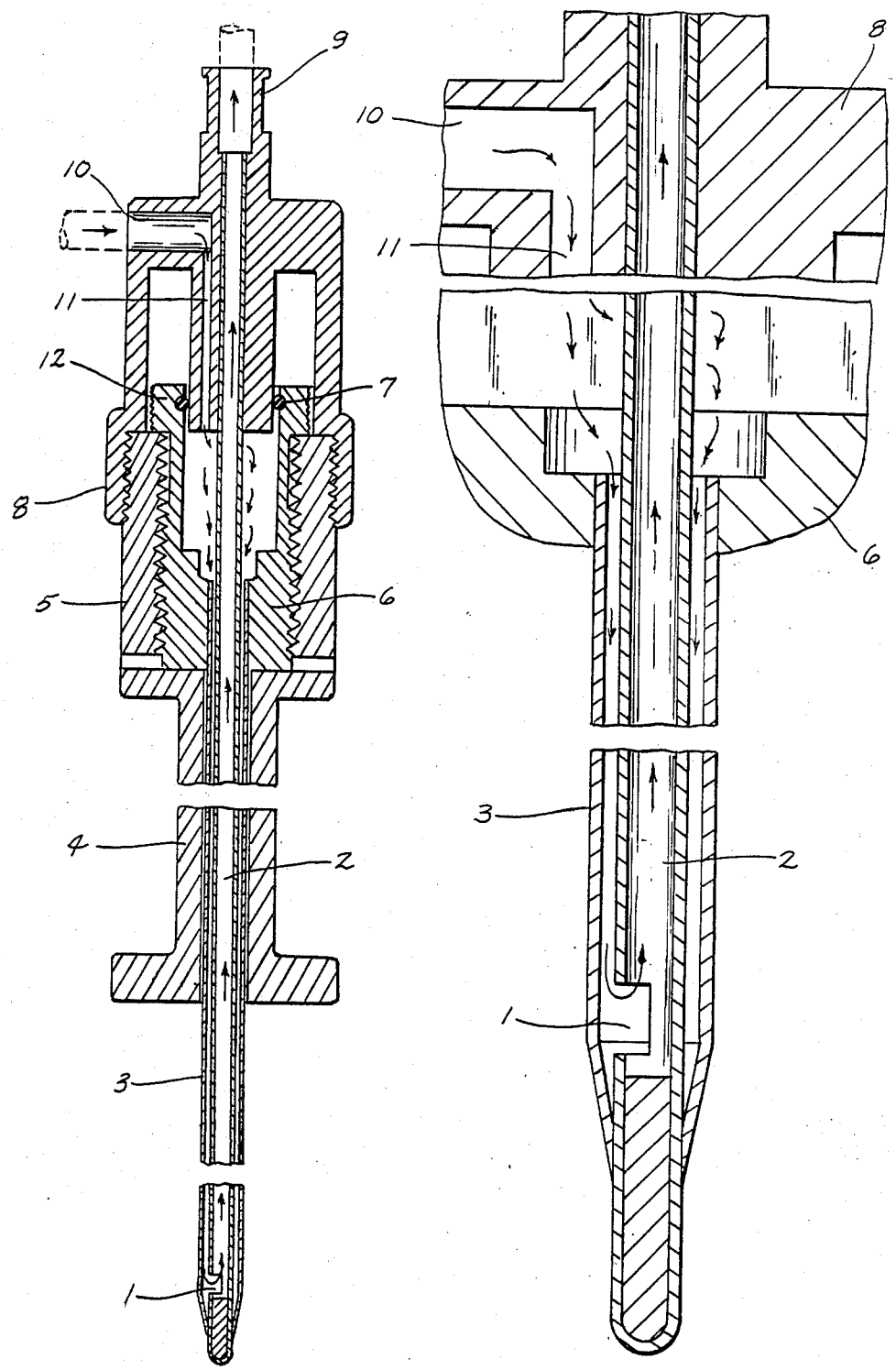

CHORION BIOPSY INSTRUMENT

TECHNICAL FIELD

The present invention relates generally to biopsy instruments and more particularly to a chorion biopsy instrument.

BACKGROUND ART

Many chromosomal and metabolic diseases of the fetus could be diagnosed before birth. Investigations could be performed if we are able to obtain fetal cells. One of the methods widely used for this purpose is amniocentesis. Amniocentesis is a minor surgical procedure during which a fine needle is inserted through the abdominal wall into the amniotic sac and a small amount of amniotic fluid is aspirated. The fetal cells from the amniotic fluid are cultured and chromosomal or biochemical investigations are performed. The results are available in about three weeks.

A new method call chorion biopsy is used in many centres and in some of them is offered as a procedure of choice. To obtain chorion tissue a small diameter tube is inserted into the uterine cavity through the cervical canal and by aspiration a small amount of chorion tissue is obtained. Chromosomal investigations could be done immediately and the results could be ready in a day or two.

Amniocentesis is usually done at about fourteen weeks gestation and when the results are available from the investigations the pregnancy will reach 17–18 weeks gestation. If the fetus is abnormal, mid-trimester abortion could be performed. However, this carries a risk of infection and bleeding, very rarely even death.

Chorion biopsy can be performed early in pregnancy, between 8 and 12 weeks gestation, and if an abnormal fetus is discovered the pregnancy can be interrupted by suction curretage. This is a much simpler and safer operation than a mid-trimester abortion.

One of the simplest and most widely used instruments consists only of a tube with a small diameter to which a syringe is attached. After the tube is inserted into the uterine cavity and suction is created, chorion tissue enters the tube. In order to obtain chorion tissue, the tube and the attached syringe are pulled out of the uterine cavity. A piece of chorion is usually retained in the tube. After the tube is taken out, it is irrigated and the chorion which is trapped inside is removed. If chorion has not been obtained, which is very often, the tube has to be reinserted.

There are optical instruments which have a guillotine-type cutting mechanism, the disadvantage of which is that the diameter is usually large and therefore insertion is not always easy. This causes trauma to the uterus and to the fetus. Another disadvantage is that the optical part becomes blurry due to bleeding that occurs during intrauterine manipulation. After the suction is applied and the tissue is cut, the whole instrument has to be removed in order to retrieve the chorion tissue. If the procedure is unsuccessful, the instrument has to be reinserted.

A chorion biopsy can also be performed by using grasping forceps. This is a very crude procedure which often perforates the membranes and causes abortions.

Consequently, there is a need for an improved chorion biopsy instrument.

DISCLOSURE OF THE INVENTION

The present invention relates to a chorion biopsy instrument for sampling chorion tissue including a housing and first and second telescoping tubes with the first tube being closed at one end thereof and having an opening one one side near the closed end. The second outer tube has a cutting edge which slides along the exterior of the first tube. A mechanism is provided for moving the second tube with respect to the first tube between a first position wherein the second tube covers the opening in the first tube and a second position wherein said second tube does not cover the opening in the first tube. A syringe is fluidly connected to a first passageway through the first tube and a bottle of culture medium is fluidly connected to a second passageway leading through the housing, between the two tubes, with the opening in the first tube connecting the first passageway to the second passageway when the tubes are in the first relative position thereof.

An object of the present invention is to provide an improved chorion biopsy instrument.

Another object is to enable chorion tissue to be obtained by cutting instead of tearing, which eliminates pulling of the chorion which could lead to separation of the chorion from the decidua and possible abortion.

A further object of the invention is the elimination of multiple insertions of the instrument, which reduces the chance of infection and trauma to the embryo and the uterus, thereby resulting in a low abortion rate.

A still further object is to provide an instrument which is very well visualized on an ultrasound screen because of its unique construction which permits fluid to flow through its tubings.

A further object is to provide an instrument which is small in diameter for facilitating easy insertion into the uterine cavity.

A still further object of the invention is to provide an instrument for obtaining a sample of chorion tissue by cutting and which is retrieved without the removal of the instrument from the uterine cavity.

Other objects, advantages, and novel features of the present invention will become apparent from the following detailed description of the invention when considered in conjunction with the accompanying drawings.

BRIEF DESCRIPTION OF THE DRAWINGS

FIG. 1 is a perspective view of a preferred embodiment of a chorion biopsy instrument constructed in accordance with the present invention;

FIG. 2 is a view taken along line 2—2 of FIG. 1;

FIG. 3 is an enlarged side elevational view of the instrument broken away to make it somewhat more compact;

FIG. 4 is a cross sectional view taken along line 4—4 of FIG. 2 showing one relative position of the moving parts of the instruments with a port on the bottom thereof open;

FIG. 5 is a cross sectional view like FIG. 4 but showing the moving parts moved so that the port on the bottom is closed; and FIG. 6 is an enlarged cross sectional view of the instrument in the FIG. 5 position showing the flow.

BEST MODE FOR CARRYING OUT THE INVENTION

Referring now to the drawings, wherein like reference numerals designate identical or corresponding parts throughout the several views, the chorion biopsy instrument shown in the drawings has two stainless steel tubes (2), (3) disposed in a housing comprised of cup (8) and cylinder (5). The smaller tube (2) slides inside the larger one (3). The proximal end of the smaller tube (2) is welded to a cup (8), and opens into a hub or connector (9). A vacuum producing device such as a syringe is attached to the hub (9) for aspiration of the chorion tissue.

The distal end of the smaller first tube (2) is plugged and is bullet-shaped. There is a side wall opening (1) with sharp edges.

The proximal end of the larger second tube (3) is welded to a piston (6). The distal and is frusto conical and the edge is razor sharp or cutting the chorion tissue and forms somewhat of a seal against the exterior of the first tube (2).

The piston (6) is screw propelled forward and backward within the cylinder (5). Rubber O-ring seal (7) seals between the piston (6) and the cup (8).

The canal (11) connects second passageway which is the space between the outer surface of the smaller tube and the inner surface of the large tube with a hub (10) for connection to a bottle of culture medium. A syringe or extension tubing (not shown) can be attached to the hub (10) for injection of culture medium.

By grasping knob (12) and rotating the piston (6) clockwise from the FIG. 4 to the FIG. 5 position thereof, the large tube (3) moves distally and covers the side wall opening (1) of the small tube (2). In this way, the space between the outer surface of the small tube (2) and the inner surface of the large one (3) is connected to the lumen of the small tube (2) through the side wall opening (1). The syringe is attached to the hub (9). An extension tubing connected to a bottle of culture medium is attached to the hub (10).

The instrument is then flushed and filled with culture medium, through hub (10). The chorion biopsy instrument is then ready for insertion into the uterine cavity through the cervical canal under ultrasound guidance.

The instrument can be well visualized on the ultrasound screen when culture medium flows through the tubings through port (10) as shown in FIGS. 5 and 6. After the instrument is properly positioned in the uterine cavity, the piston (6) is turned counterclockwise from the FIG. 5 to the FIG. 4 position, which moves the large tube (3) backwards and the side wall opening (1)is then exposed as shown in FIG. 4. By pulling the piston of the syringe (not shown) attached to the hub (9), a negative pressure is created at the side wall opening (1), and chorion tissue is sucked into the small tube (2) as shown in FIG. 4. The piston (6) is then rotated clockwise from the FIG. 4 to the FIG. 5 position. The sharp edge of the large tube moves forward and cuts the chorion tissue at the level of the side wall opening (1). When the large tube (3) moves to its most distal position (FIGS. 5 and 6) (which is close to the tip of the small tube), culture medium rushes between the two tubes (2), (3) through the side wall opening (1) and propels the chorion tissue towards the syringe (not shown) which is attached to the hub (9). The recovered tissue is immediately checked under a microscope. If the first attempt is unsuccessful, the position of the instrument can be readjusted and the procedure may be repeated until chorion tissue is obtained. This does not necessitate the removal of the instrument from the uterine cavity.

Obviously, many modifications and variations of the present invention are possible in light of the above teachings. It is therefore to be understood that, within the scope of the appended claims, the invention may be practiced otherwise than as specifically described.

I claim:

1. A chorion biopsy instrument comprising:

a housing;

a first elongated tube operably attached to said housing, said first tube having a first passageway therein, said first tube being closed at one end thereof and having an opening in one side thereof adjacent to said one end, said opening being in fluid communication with said first passageway;

means attached to said housing for fluidly connecting a vacuum producing device to said first passageway;

a second elongated tube telescopically disposed over said first tube, said second tube having a large enough internal diameter to form a second passageway between the inside of the second tube and exterior of the first tube;

means attached to one end of the second tube for fluidly sealing to some extent against the exterior of the first tube;

means connected to said housing in fluid communication with said second passageway for connection to a reservoir of culture medium; and positioning means operably attached to said housing and to said first and second tubes for reciprocally moving one of said first and second tubes with respect to the other between a first relative position wherein said opening in the side of the first tube is covered by said second tube and is therefore in fluid communication with said second passageway and a second position wherein said second tube does not cover said opening in the first tube whereby the first and second tubes can be inserted into the uterine cavity through the cervical canal while in the first position thereof, a chorion tissue culture can be taken while moving the tubes to the second relative position thereof and a culture medium can be pulled through the second passageway by suction from action of the vacuum producing device to carry the chorion tissue through the opening in the first passageway to the syringe for testing.

2. The instrument of claim 1 wherein said one edge of the second tube is sharpened for cutting chorion tissue when said second tube is moved with respect to the first tube while abutting chorion tissue.

3. The instrument of claim 2 wherein said positioning means comprises a threaded piston threadably engaging said housing and rigidly connected to said second tube whereby rotation of said piston in one rotary direction moves said second tube toward the first position thereof with respect to the first tube and rotation of the piston in the other rotary direction moves the second tube toward the second position thereof relative to said first tube.

4. The apparatus of claim 3 wherein said housing has two parts threaded together and one of said parts includes a support means for guidingly supporting the first and second tubes.

* * * * *